United States Patent
Pan et al.

(10) Patent No.: US 12,383,189 B2
(45) Date of Patent: Aug. 12, 2025

(54) METHOD FOR EXTRACTING NEUROIMAGING BIOMARKER BASED ON INTERPRETABLE ENSEMBLE 3DCNN

(71) Applicant: GUANGDONG UNIVERSITY OF TECHNOLOGY, Guangdong (CN)

(72) Inventors: Dan Pan, Guangdong (CN); An Zeng, Guangdong (CN); Baoyao Yang, Guangdong (CN)

(73) Assignee: GUANGDONG UNIVERSITY OF TECHNOLOGY, Guangdong (CN)

( * ) Notice: Subject to any disclaimer, the term of this patent is extended or adjusted under 35 U.S.C. 154(b) by 141 days.

(21) Appl. No.: 18/450,338

(22) Filed: Aug. 15, 2023

(65) Prior Publication Data
US 2024/0057932 A1    Feb. 22, 2024

(30) Foreign Application Priority Data
Aug. 16, 2022    (CN) .......................... 202210978102.5

(51) Int. Cl.
*A61B 5/00*    (2006.01)
*A61B 5/055*    (2006.01)
(Continued)

(52) U.S. Cl.
CPC ............ *A61B 5/4088* (2013.01); *A61B 5/055* (2013.01); *G06T 5/70* (2024.01); *G06T 7/0012* (2013.01);
(Continued)

(58) Field of Classification Search
CPC ..... A61B 5/055; A61B 5/0042; A61B 5/7267; G06N 3/08; G06N 20/20; G06V 2201/03;
(Continued)

(56) References Cited

U.S. PATENT DOCUMENTS

2022/0051801 A1*    2/2022    Feng .................... G06T 7/0012

FOREIGN PATENT DOCUMENTS

| CN | 109165667 | 1/2019 |
| CN | 113951830 | 1/2022 |

OTHER PUBLICATIONS

Alzheimer's Disease Detection Through Whole-Brain 3D-CNN MRI by G. Folego et al. Frontiers in Bioengineering and Biotechnology. (Year: 2020).*
Early Detection of Alzheimers Disease Using Magnetic Resonance Imaging: A Novel Approach Combining Convolution Neural Networks and Ensemble Learning by D. Pan et al. Frontiers in Neuroscience. vol. 14, Article 259. (Year: 2020).*
(Continued)

*Primary Examiner* — Jason M Ip
(74) *Attorney, Agent, or Firm* — JCIPRNET

(57) ABSTRACT

The present invention provides a method for extracting a neuroimaging biomarker based on an interpretable ensemble three-dimensional convolutional neural network (3DCNN) to address limitations in the prior art. The present invention derives a novel neuroimaging biomarker P-score from prediction results obtained by an ensemble three-dimensional convolutional neural network model. The solution can help researchers to conduct studies on longitudinal trajectory changes of structural magnetic resonance imaging (sMRI) during the progression of Alzheimer's disease, and analyze an association of the longitudinal trajectory changes with neurodegenerative changes of Alzheimer's disease subjects. The extracted neuroimaging biomarker can provide a basis for predicting a sequence of intervention of brain regions in the neurodegenerative changes of Alzheimer's disease patients and upcoming clinical symptoms.

16 Claims, 4 Drawing Sheets

(51) Int. Cl.
　　*G06T 5/70*　　　(2024.01)
　　*G06T 7/00*　　　(2017.01)
　　*G06T 7/11*　　　(2017.01)
　　*G06V 10/764*　　(2022.01)

(52) U.S. Cl.
　　CPC .............. *G06T 7/11* (2017.01); *G06V 10/764* (2022.01); *G06T 2207/20084* (2013.01); *G06T 2207/30016* (2013.01)

(58) Field of Classification Search
　　CPC ......... G06V 10/82; G06T 5/70; G06T 7/0012; G06T 7/11; G06T 2207/20084; G06T 2207/30016; G06T 2207/10088; G06T 2207/20076
　　See application file for complete search history.

(56) References Cited

OTHER PUBLICATIONS

Diagnosis of Alzheimers Disease with Ensemble Learning Classifier and 3D Convolutional Neural Network by P. Zhang et al. Sensors. (Year: 2021).*

Early Identification of Alzheimers Disease Using an Ensemble of 3D Convolutional Neural Networks and Magnetic Resonance Imaging by Y. Chen et al. J Ren. pp. 303-311. (Year: 2018).*

Construction of MRI-Based Alzheimers Disease Score Based on Efficient 3D Convolutional Neural Network: Comprehensive Validation on 7902 Images from a Multi-Center Dataset by E. Yee et al. J Alzheimerâs Disease. 79, 47-58. (Year: 2021).*

* cited by examiner

METHOD FOR EXTRACTING NEUROIMAGING BIOMARKER BASED ON INTERPRETABLE ENSEMBLE 3DCNN

CROSS-REFERENCE TO RELATED APPLICATION

This application claims the priority benefit of Chinese application serial no. 202210978102.5, filed on Aug. 16, 2022. The entirety of the above-mentioned patent application is hereby incorporated by reference herein and made a part of this specification.

TECHNICAL FIELD

The present invention relates to the technical field of medical image data analysis, in particular to the application of machine learning in the technical field of medical image data analysis, and more particularly, relates to a method for extracting a neuroimaging biomarker based on an interpretable ensemble 3DCNN.

BACKGROUND

Data analysis of brain images is crucial to the study of Alzheimer's disease (AD). Although there are various technical supports for the acquisition of brain images, such as positron emission tomography (PET) and magnetic resonance imaging (MRI), due to the high cost of PET, PET imaging is not as widely used in practice as MRI imaging which is low-cost and non-invasive. Therefore, it is necessary to improve data analysis technology of MRI imaging.

Over the past decade, machine learning (ML) has been used for analysis of brain MRI imaging. However, taking the Chinese invention application: biological classification device and method for alzheimer's disease using brain image, filed on Apr. 15, 2022 as an example, most of existing ML applications are focused on implementing classification tasks, rather than analyzing a progression pattern of neurodegenerative changes based on neuroimaging.

Recently, some studies have begun to attempt to extract atrophy features or patterns from structural magnetic resonance imaging (sMRI images) to infer brain age. Although ML methods using independent training strategies and voting ensemble rules may support an association between neuroimaging phenotypes and neurodegenerative progression in Alzheimer's disease, longitudinal trajectory changes of sMRI images during the progression of Alzheimer's disease, such as spatial and temporal associations between neurodegenerative brain regions, have not been studied. Therefore, there are still some limitations in the prior art.

SUMMARY

In order to address the limitations in the prior art, the present invention provides a method for extracting a neuroimaging biomarker based on an interpretable ensemble 3DCNN. The technical solutions adopted by the present invention are as follows:

A method for extracting a neuroimaging biomarker based on an interpretable ensemble 3DCNN includes the following steps:

S1, acquiring an sMRI image to be processed, and preprocessing the sMRI image;

S2, segmenting the preprocessed sMRI image into a plurality of small cubes;

S3, inputting the small cubes into an ensemble 3DCNN model trained on a preset sMRI dataset to obtain a prediction probability of each of the small cubes as to whether the sMRI image belongs to an Alzheimer's disease patient; and S4, converting the prediction probability into a neuroimaging biomarker P-score for the sMRI image.

As a preferred solution, the preprocessing includes skull extraction, MNI space registration, image smoothing, and image normalization.

As a preferred solution, the ensemble 3DCNN model includes a plurality of base classifiers and a meta-classifier, where the base classifiers are 3DCNN models; and the meta-classifier includes a one-dimensional convolutional layer and a fully connected layer in sequence.

Further, a neuroimaging biomarker P-score$_{cube}$ of the sMRI image at a small cube level is obtained by:

$$\text{P-score}_{cube}(i,c) = w_{ic} \times p_{ic},$$

where i denotes an index of the sMRI image, c denotes an index of a small cube, $p_{ic}$ denotes a prediction probability as to whether the sMRI image belongs to an Alzheimer's disease patient obtained by a base classifier corresponding to the small cube (i, c), and w denotes a weight of the one-dimensional convolutional layer in the meta-classifier corresponding to the base classifier.

Furthermore, a neuroimaging biomarker P-score$_{voxel}$ of the sMRI image at a voxel level is obtained by:

evenly dividing, by voxels of a brain tissue in a small cube, P-score$_{cube}$ of the small cube where the voxels are located, that is, P-score$_{voxel}$=P-score$_{cube}$/M, where M denotes the quantity of the voxels of the brain tissue in the small cube; and setting a P-score$_{voxel}$ value of voxels of a non-brain tissue in the small cube to be 0.

Furthermore, a neuroimaging biomarker P-score$_{region}$ of the sMRI image at a brain region level is obtained by:

dividing a sum of P-score$_{voxel}$ of all voxels in the brain region by the quantity of the voxels included in the brain region.

Furthermore, a neuroimaging biomarker P-score$_{whole}$(i) of the sMRI image at a whole-brain level is obtained by:

scaling a value domain of P-score$_{region}$ of each brain region to a range of [0,1] by normalization; and aggregating the P-score$_{region}$ of each brain region after the normalization to obtain P-score$_{whole}$ of a whole brain as follows:

$$\text{P-score}_{whole}(i) = \Sigma_k \text{P-score}_{region}(i,k),$$

where i denotes the index of the sMRI image, and k denotes an index of the brain region.

The present invention further includes the following contents:

A system for extracting a neuroimaging biomarker based on an interpretable ensemble 3DCNN includes an image acquisition and preprocessing module, an image segmentation module, a prediction probability acquisition module, and a prediction probability conversion module which are connected in sequence, wherein the image acquisition and preprocessing module is configured to acquire an sMRI image to be processed and preprocess the sMRI image;

the image segmentation module is configured to segment the preprocessed sMRI image into a plurality of small cubes;

the prediction probability acquisition module is configured to input the small cubes into an ensemble 3DCNN model trained on a preset sMRI dataset to obtain a prediction probability of each of the small cubes as to whether the sMRI image belongs to an Alzheimer's disease patient; and the prediction probability conversion module is configured to convert the prediction probability into a neuroimaging biomarker P-score for the sMRI image.

A storage medium having a computer program stored on the storage medium is provided. The computer program, when executed by a processor, implements the steps of the above method for extracting the neuroimaging biomarker based on the interpretable ensemble 3DCNN.

A computer device includes a storage medium, a processor, and a computer program stored in the storage medium and executable by the processor. The computer program, when executed by the processor, implements the steps of the above method for extracting the neuroimaging biomarker based on the interpretable ensemble 3DCNN.

DETAILED DESCRIPTION OF EMBODIMENTS

The accompanying drawings are for illustrative purposes merely and should not be construed as limitations on this patent.

It should be noted that the described embodiments are merely a part of the embodiments of the present application, rather than all the embodiments. Based on the embodiments of the present application, all other embodiments obtained by a person of ordinary skill in the art without making creative effort fall within the scope of protection of the embodiments of the present application.

The terms used in the embodiments of the present application are merely for the purpose of describing specific embodiments, and not intended to limit the embodiments of the present application. The singular forms "one", "said" and "the" used in the embodiments of the present application and the appended claims are also intended to include the plural form unless the context clearly indicates other meanings. It should also be understood that the term "and/or" as used herein refers to and includes any or all possible combinations of one or more associated listed items.

When the following description refers to the accompanying drawings, unless otherwise indicated, the same numbers in different accompanying drawings indicate the same or similar elements. The implementations described in the following exemplary embodiments do not represent all implementations consistent with the present application. Rather, they are merely instances of apparatuses and methods consistent with some aspects of the present application as detailed in the appended claims. In the description of the present application, it is to be understood that the terms "first", "second", "third", etc. are used only to distinguish similar objects and need not be used to describe a particular order or sequence, nor are they to be understood as indicative of or suggestive of relative importance. For a person of ordinary skill in the art, the specific meaning of the above-mentioned terms in the present application may be understood according to specific situations.

Furthermore, in the description of the present application, unless otherwise indicated, "a plurality of" means two or more. "And/or" describes the association relationship of associated objects, which means that three relationships may exist. For example, A and/or B may mean three cases: A alone, A and B at the same time, and B alone. The character "/" generally indicates that associated objects are in an "or" relationship. The present invention is further described below in conjunction with the accompanying drawings and embodiments.

In order to address the limitations in the prior art, this embodiment provides a technical solution, and the technical solution of the present invention is further described below in conjunction with the accompanying drawings and embodiments.

Embodiment 1

Figure 1:
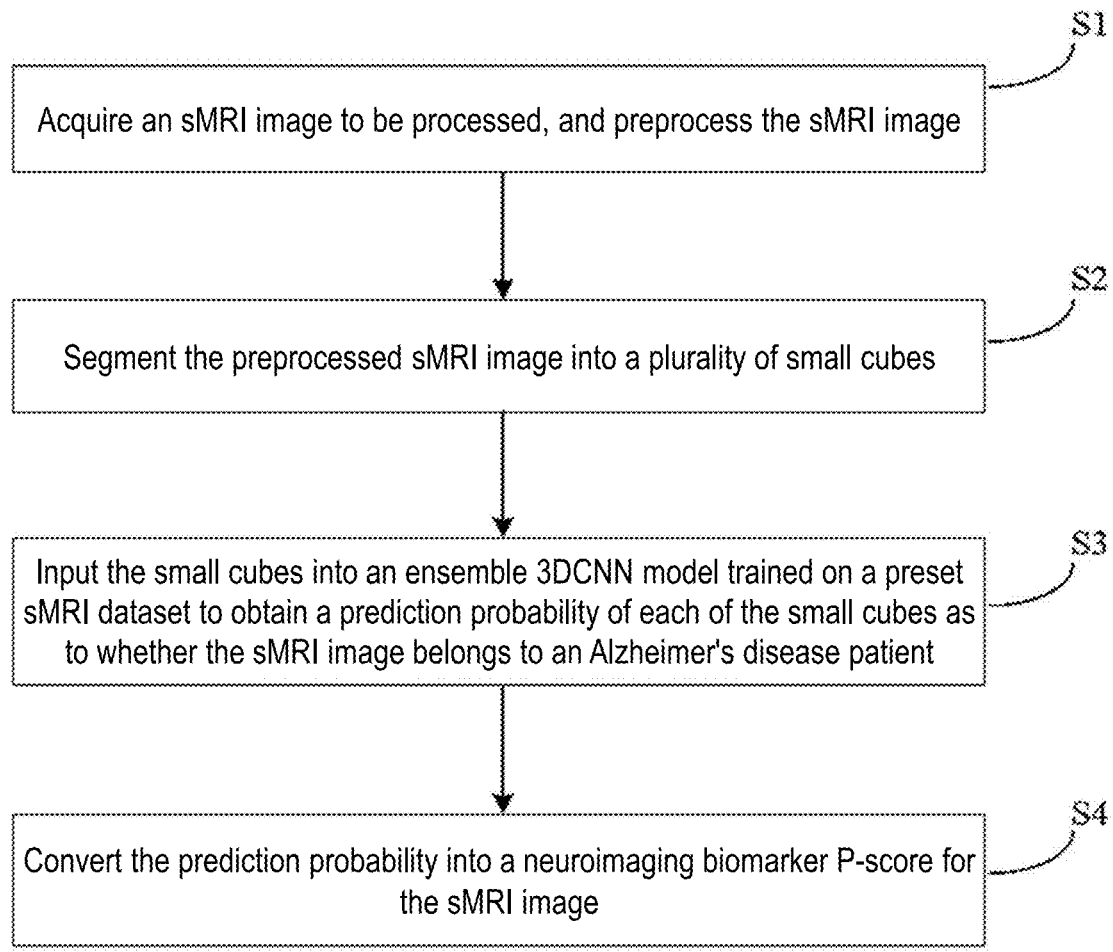
FIG. 1 is a schematic diagram of steps of a method for extracting a neuroimaging biomarker based on an interpretable ensemble 3DCNN according to Embodiment 1 of the present invention.

Referring to FIG. 1, a method for extracting a neuroimaging biomarker based on an interpretable ensemble 3DCNN includes the following steps:

S1, acquire an sMRI image to be processed, and preprocess the sMRI image;

S2, segment the preprocessed sMRI image into a plurality of small cubes;

S3, input the small cubes into an ensemble 3DCNN model trained on a preset sMRI dataset to obtain a prediction probability of each of the small cubes as to whether the sMRI image belongs to an Alzheimer's disease patient; and S4, convert the prediction probability into a neuroimaging biomarker P-score for the sMRI image.

Compared with the prior art, the present invention derives a novel neuroimaging biomarker P-score from prediction results obtained by the ensemble 3DCNN model. The solution may help researchers to conduct studies on longitudinal trajectory changes of sMRI images during the progression of Alzheimer's disease, and analyze an association of the longitudinal trajectory changes with neurodegenerative changes of Alzheimer's disease subjects. The extracted neuroimaging biomarker may provide a basis for predicting a sequence of intervention of brain regions in the neurodegenerative changes of an Alzheimer's disease patient and upcoming clinical symptoms.

Specifically, the 3DCNN refers to a three-dimensional convolutional neural network. The present invention aims to enable researchers to explore less obvious details of sMRI images associated with Alzheimer's disease through a machine learning model and analyze the longitudinal trajectory changes of the sMRI images during the progression of Alzheimer's disease, that is, to analyze changes of sMRI images at a plurality of time points in the progression of Alzheimer's disease.

The neuroimaging biomarker P-score may be regarded as a quantitative index reflecting the degree of neurodegenerative changes.

As a preferred embodiment, the preprocessing includes skull extraction, MNI space registration, image smoothing, and image normalization.

Specifically, skull extraction, MNI space registration, and image smoothing may be performed by using default settings in a tool Computational Anatomy Toolbox (CAT12, dbm.neuro.unijena.de/cat/), and then each image is normalized to a tensor of size 121×145×121. The spatial resolution of the tensor is 1.5×1.5×1.5 mm³ per voxel, and a value range of the voxels is from 0 to 1. Each sMRI image is segmented into non-overlapping small cubes of size 25×25×25, whereby each sMRI image may obtain 150 small cubes.

Figure 2:
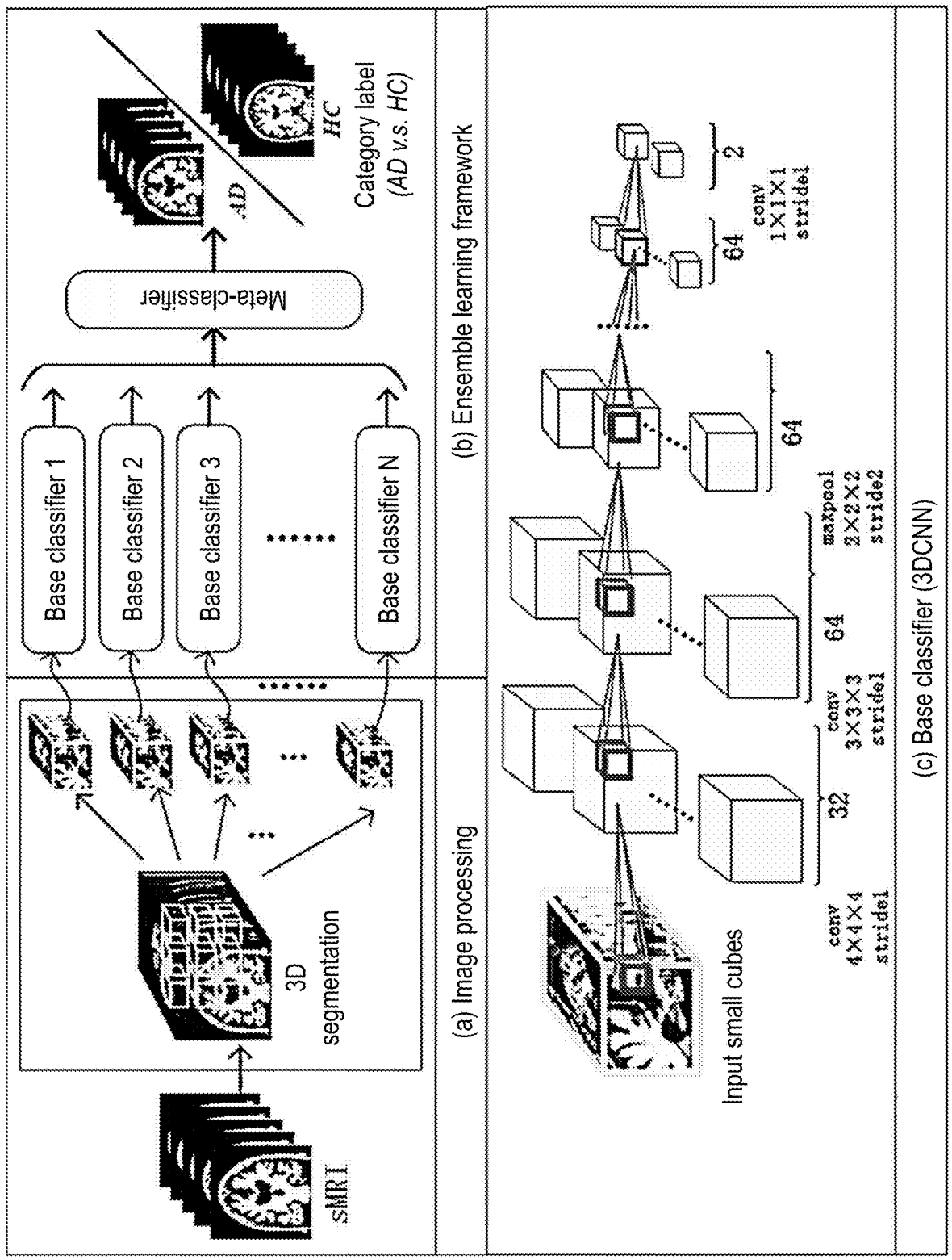
FIG. 2 is a schematic block diagram of an ensemble 3DCNN model according to the present invention.

As a preferred embodiment, referring to FIG. 2, the ensemble 3DCNN model includes a plurality of base classifiers and a meta-classifier. The base classifiers are 3DCNN models. The meta-classifier includes a one-dimensional convolutional layer and a fully connected layer in sequence.

Specifically, when the ensemble 3DCNN model is trained, the above-mentioned preprocessing and segmenting operations also need to be carried out on images in the sMRI dataset.

Accordingly, the quantity of the base classifiers is consistent with the quantity of small cubes to be segmented from each sMRI image, which is 150, and the 150 small cubes are used as inputs of the 150 base classifiers respectively. As shown in region (c) of FIG. 2, each of the base classifiers is a 3DCNN model consisting of 7 layers such that an input with a size of 25×25×25 is transformed to a one-dimensional vector representing features of the small cubes with a length of 64, and then is transformed to a two-dimensional vector representing a probability of each small cube as an Alzheimer's disease patient (AD class) and a healthy care person (HC class). The base classifiers are trained independently on the corresponding 150 small cubes in training set data in the sMRI dataset respectively.

During the training, the base classifiers and the meta-classifier are trained separately. After the base classifiers are trained, N (for example, 35) base classifiers with the best performance in validation set data of the sMRI dataset may be selected, and output features thereof are concatenated and inputted into the meta-classifier, that is, a size of the feature that have been concatenated is N×64, where N denotes the quantity of the selected base classifiers. The meta-classifier includes the one-dimensional convolutional layer and the fully connected layer, and a size of a convolutional kernel of the one-dimensional convolutional layer is the quantity N of the concatenated features of the base classifiers. Due to a computational method of one-dimensional convolution, each weight of the one-dimensional convolution corresponds to each of the base classifiers respectively. Guided by a disease label, the meta-classifier learns on the dataset by using the data of the concatenated output features of the base classifiers. An output of the meta-classifier, as a final output of the ensemble 3DCNN, is a two-dimensional vector. Two values in the vector correspond to a probability of a current input sMRI image belonging to an Alzheimer's disease patient (class AD) and a probability of a current input sMRI image belonging to a health care person (HC class), that is, the model provides prediction scores for an Alzheimer's disease patient (AD class) and a health care person (HC class).

Figure 3:
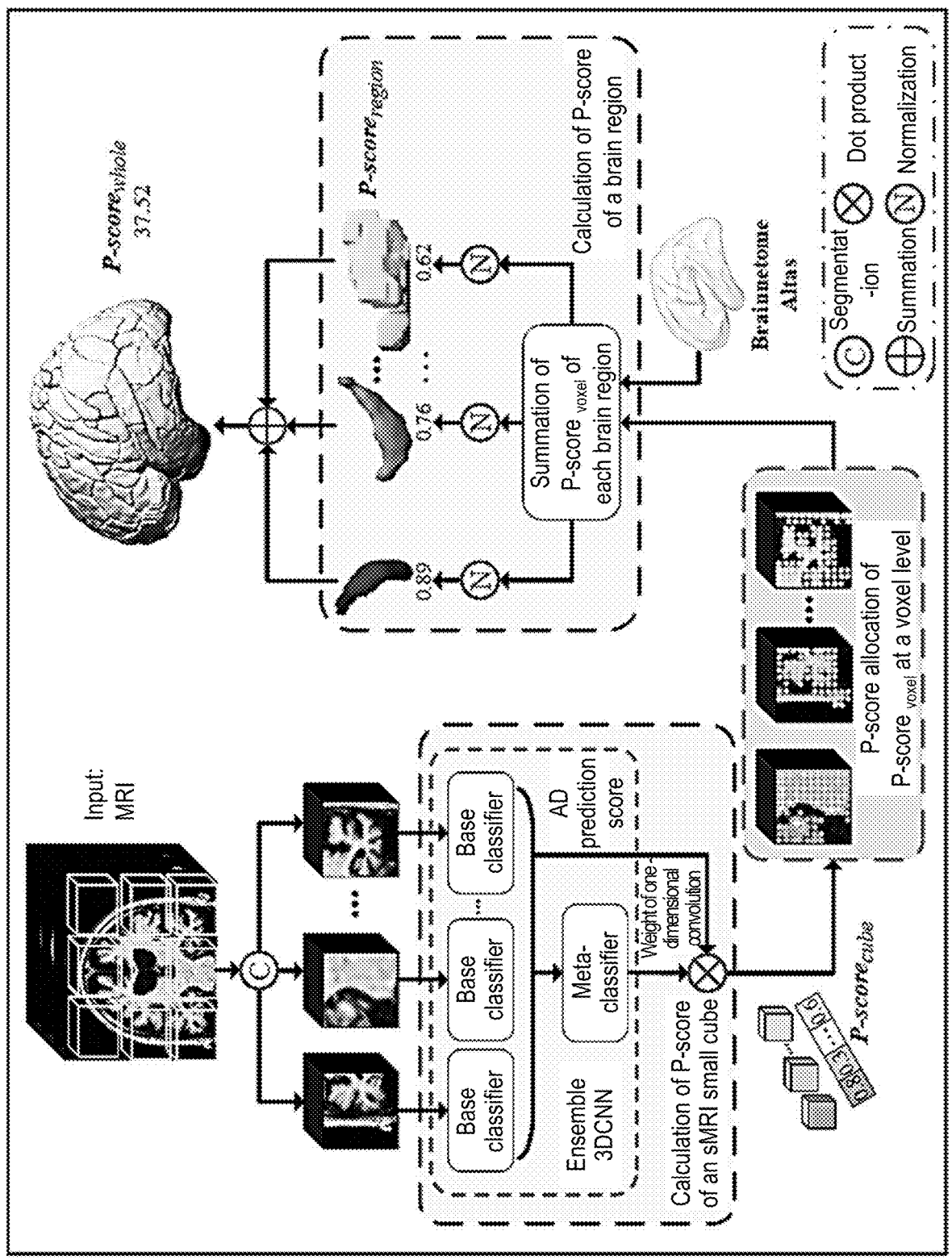
FIG. 3 is a schematic diagram of a relationship between P-score adopted by the present invention at different levels.

The neuroimaging biomarker P-score is a multilevel measurement method that may evaluate neurodegenerative changes at four levels (that is, a voxel level, a region level, a small cube level, and a whole-brain level). The higher a P-score value, the higher the degree of neurodegenerative changes. FIG. 3 shows a relationship between P-score values at the four levels.

Further, a neuroimaging biomarker P-score$_{cube}$ of the sMRI image at the small cube level is obtained by:

$$P\text{-score}_{cube}(i,c) = w_{ic} \times p_{ic},$$

where i denotes an index of the sMRI image, c denotes an index of a small cube, $p_{ic}$ denotes a prediction probability as to whether the sMRI image belongs to an Alzheimer's disease patient obtained by a base classifier corresponding to the small cube (i, c), and w denotes a weight of the one-dimensional convolutional layer in the meta-classifier corresponding to the base classifier.

Thus, the neuroimaging biomarker P-score$_{cube}$ of the sMRI image at the small cube level may be obtained directly after inputting the small cube into the ensemble 3DCNN model trained on the preset sMRI dataset.

Furthermore, a neuroimaging biomarker P-score$_{voxel}$ of the sMRI image at the voxel level is obtained by:
evenly dividing, by voxels of a brain tissue in a small cube, P-score$_{cube}$ of the small cube where the voxels are located, that is, P-score$_{voxel}$=P-score$_{cube}$/M, where M denotes the quantity of the voxels of the brain tissue in the small cube; and setting a P-score$_{voxel}$ value of voxels of a non-brain tissue in the small cube to be 0.

Furthermore, a neuroimaging biomarker P-score$_{region}$ of the sMRI image at the brain region level is obtained by:
dividing a sum of P-score$_{voxel}$ of all voxels in a brain region by the quantity of the voxels included in the brain region.

Specifically, according to divisions in Brainnetome Atlas, a human brain is divided into 246 regions that reflect anatomical and functional connections throughout the whole brain. Each brain region may also be evaluated with corresponding P-score$_{region}$, and P-score$_{region}$ of each brain region is derived based on P-score$_{voxel}$ of voxels included in the brain region. To calculate P-score$_{region}$ of a brain region, a sum of P-score$_{voxel}$ of all voxels of the brain region is obtained firstly, then the sum is divided by the size of the brain region, that is, the quantity of the voxels included in the brain region, thereby eliminating the influence of the size difference between the different brain regions on P-score$_{region}$.

Furthermore, a neuroimaging biomarker P-score$_{whole}$(i) of the sMRI image at the whole-brain level is obtained by:
scaling a value range of P-score$_{region}$ of each brain region to a range of [0,1] by normalization; and aggregating the P-score$_{region}$ of each brain region after the normalization to obtain P-score$_{whole}$ of a whole brain as follows:

$$P\text{-score}_{whole}(i) = \Sigma_k P\text{-score}_{region}(i,k),$$

where i denotes the index of the sMRI image, and k denotes an index of the brain region.

Figure 4:
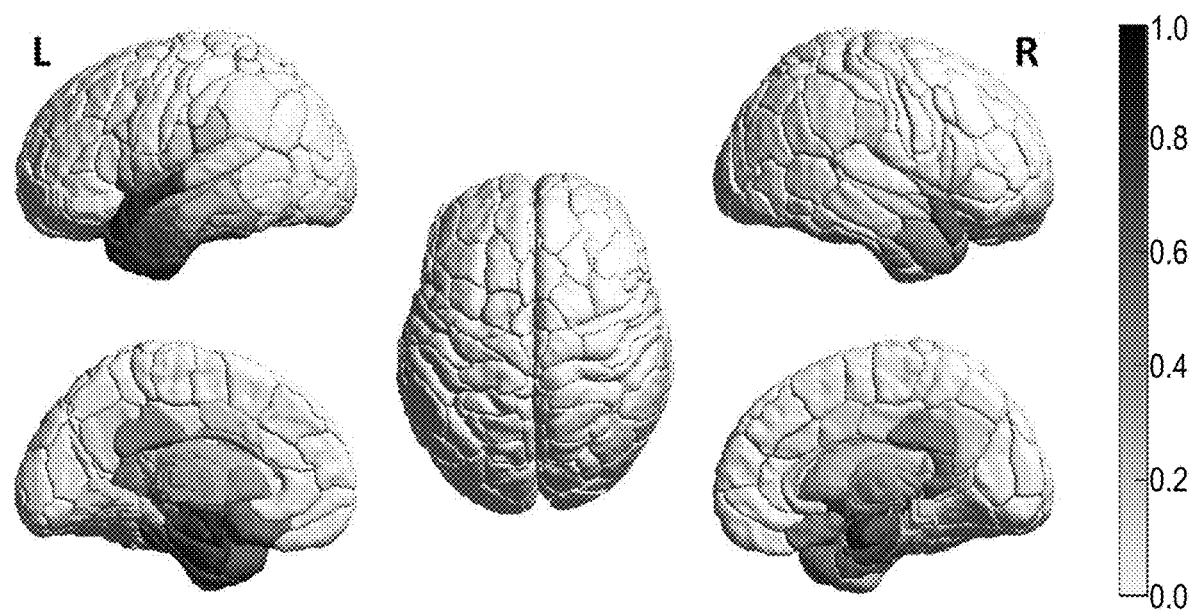
FIG. 4 is an example of a neuroimaging biomarker P-score extracted by an ML model from a sMRI image of the brain of an Alzheimer's disease subjects according to the present invention.

Specifically, the value range of P-score$_{region}$ of each brain may be scaled to the range of [0,1] by Min-Max normalization. Referring to an example shown in FIG. 4, the darker the color, the higher P-score; and the higher P-score of the brain, the higher the degree of neurodegenerative changes. Thus, P-score of each brain region in the sMRI image of the brain of an Alzheimer's disease subject may be visually illustrated, indicating that the degree of neurodegenerative changes varies according to brain region.

Next, the solution of this embodiment will be further illustrated by using an sMRI image sequence at a plurality of time points obtained from an ADNI database.

Referring to Table 1:

TABLE 1

Statistical information of sMRI images of subjects in different stages of a study

| Dataset | Category | Quantity of subjects with a different quantity of sMRI images in a longitudinal image sequence thereof | | | | | | | | | | | | | Quantity of sMRI Condition | |
|---|---|---|---|---|---|---|---|---|---|---|---|---|---|---|---|---|
| | | 1 | 2 | 3 | 4 | 5 | 6 | 7 | 8 | 9 | 10 | 11 | Total | ≥2 | Total | 1 |
| Training set (ADNI) | AD | 14 | 13 | 30 | 65 | 5 | 1 | 3 | 5 | — | — | — | 136 | 122 | 482 | 468 |
| | HC | 7 | 10 | 13 | 27 | 51 | 33 | 7 | 4 | 7 | 2 | 1 | 162 | 155 | 802 | 795 |
| Validation set (ADNI) | AD | 15 | 16 | 12 | 42 | 13 | 2 | — | 1 | — | — | — | 101 | 86 | 336 | 321 |
| | HC | 5 | 1 | 7 | 17 | 23 | 33 | 2 | 4 | 3 | 2 | 3 | 100 | 95 | 535 | 530 |
| Alzheimer's disease for analysis (ADNI) | All samples | 29 | 29 | 42 | 107 | 18 | 33 | 3 | 6 | — | — | — | 237 | 208 | 818 | 789 |
| | Meeting condition 2 | 24 | 25 | 37 | 96 | 16 | 3 | 3 | 4 | — | — | — | 208 | 184 | 720 | 696 |
| | Meeting condition 2 and 3 | 0 | 22 | 33 | 86 | 16 | 3 | 3 | 4 | — | — | — | 167 | 167 | 638 | 638 |
| Test set (OASIS) | AD All samples | 208 | 42 | 3 | — | — | — | — | — | — | — | — | 253 | 45 | 301 | 93 |
| | AD Meeting condition 2 | 155 | 24 | 2 | — | — | — | — | — | — | — | — | 181 | 26 | 209 | 54 |
| | AD (Meeting conditions 2 and 3) | 155 | 20 | 2 | — | — | — | — | — | — | — | — | 181 | 22 | 209 | 46 |
| | HC | 102 | 76 | 38 | 17 | 7 | 9 | 4 | — | — | — | — | 253 | — | — | — |

Note:
Condition 1: The longitudinal image sequence includes sMRI images obtained at not less than two time points.
Condition 2: The ensemble 3DCNN correctly classifies all images in the longitudinal sequence of a subject.
Condition 3: At least one brain region is marked as degenerative by the neuroimaging biomarker.
Criterion 1: The longitudinal image sequence includes sMRI images at not less than two time points.
Criterion 2: The ensemble 3DCNN correctly classifies all images in a longitudinal image sequence of a subject.
Criterion 3: At least one brain region in the longitudinal image sequence of the subject is marked as a neurodegenerative change by the neuroimaging biomarker P-score.
*: For 253 HC subjects in the test dataset shown in Table 1, longitudinal image sequences were not used in a pattern analysis stage of the study.

According to statistical data in Table 1, the ensemble 3DCNN model correctly identified 720 of 818 sMRI images of Alzheimer's disease symptoms in the ADNI database. A brain region has a high probability of being unrelated to neurodegenerative changes associated with the progression of Alzheimer's disease if a P-score value of the brain region is lower than $\lambda=0.73$, where the value of $\lambda$ is determined by a mean value and a standard deviation (std) of P-score of all brain regions in sMRI images of Alzheimer's disease patients that were correctly identified by the ensemble 3DCNN, where $\lambda=\text{mean}(P\text{-score})+2\text{std}=0.73$ here. Thus, a brain region meeting P-score>$\lambda$ may be considered as a neurodegenerative brain region.

An analysis result showed that the left medial amygdala (L.mAmyg), the left nucleus accumbens (L.NAC), and the left lateral amygdala (L.lAmyg) were the most commonly affected regions in the progression of Alzheimer's disease. Specifically, in 638 sMRI images of Alzheimer's disease patients, 82.60%, 80.72%, and 73.20% were scored as having neurodegeneration in these three brain regions respectively.

Frequencies of the corresponding brain regions in the 638 sMRI images labeled as Alzheimer's disease are presented in Table 2 as the probabilities of neurodegenerative changes of these brain regions during the progression of Alzheimer's disease in patients with Alzheimer's disease. The results showed that most of these common brain regions with neurodegenerative changes were located in the basal portion of the putamen and the nucleus accumbens, which is consistent with Braak's report [Braak, H. & Braak, E. Neuropathological staging of alzheimer-related changes. Acta neuropathologica 82, 239-259 (1991)] for amyloid deposition, and in addition, brain regions with high P-score, such as the amygdala, granular insular cortex, and hippocampus roughly match the isocortex, basal magnocellular complex, and transentorhinal regions identified in Braak's report.

TABLE 2

Frequencies of neurodegenerative brain regions in 638 sMRI images of Alzheimer's disease patients

| Ranking | Set | Frequent item |
|---|---|---|
| 1 | { L.mAmyg } | 82.60% |
| 2 | { L.NAC } | 80.72% |
| 3 | { L.mAmyg, L.NAC } | 79.00% |
| 4 | { L.lAmyg } | 73.20% |
| 5 | { L.vIa } | 71.79% |
| 6 | { L.vIa, L.lAmyg } | 71.79% |
| 7 | { L.mAmyg, L.lAmyg } | 70.53% |
| 8 | { L.vIa, L.mAmyg } | 69.28% |
| 9 | { L.vId/vIg } | 68.50% |
| 10 | { L.vIa, L.vId/vIg } | 68.50% |
| 11 | { LvId/vIg, L.lAmyg } | 68.50% |
| 12 | { L.vIa, L.vId/vIg, L.lAmyg } | 68.50% |
| 13 | { L.TI } | 67.87% |

TABLE 2-continued

Frequencies of neurodegenerative brain regions in 638 sMRI images of Alzheimer's disease patients

| Ranking | Set | Frequent item |
|---|---|---|
| 14 | { L.TI, L.vIa } | 67.87% |
| 15 | { L.TI, L.lAmyg } | 67.87% |
| 16 | { L.TI, L.vIa, L.lAmyg } | 67.87% |
| 17 | { L.TI, L.vId/vIg } | 66.93% |
| 18 | { L.lAmyg, L.NAC } | 66.93% |
| 19 | { L.TI, L.vIa, L.vId/vIg , L.lAmyg } | 66.93% |
| 20 | { L.mAmyg, L.lAmyg, L.NAC } | 66.93% |

Embodiment 2

Figure 5:
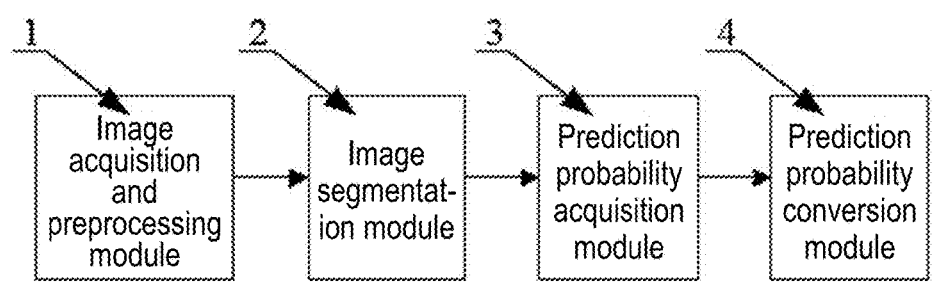
FIG. 5 is a schematic diagram of a system for extracting a neuroimaging biomarker based on an interpretable ensemble 3DCNN according to Embodiment 2 of the present invention.

Referring to FIG. 5, a system for extracting a neuroimaging biomarker based on an interpretable ensemble 3DCNN includes an image acquisition and preprocessing module 1, an image segmentation module 2, a prediction probability acquisition module 3, and a prediction probability conversion module 4 which are connected in sequence.

The image acquisition and preprocessing module 1 is configured to acquire an sMRI image to be processed and preprocess the sMRI image.

The image segmentation module 2 is configured to segment the preprocessed sMRI image into a plurality of small cubes.

The prediction probability acquisition module 3 is configured to input the small cubes into an ensemble 3DCNN model trained on a preset sMRI dataset to obtain a prediction probability of each of the small cubes as to whether the sMRI image belongs to an Alzheimer's disease patient.

The prediction probability conversion module 4 is configured to convert the prediction probability into a neuroimaging biomarker P-score for the sMRI image.

Embodiment 3

A storage medium having a computer program stored on the storage medium is provided. The computer program, when executed by a processor, implements the steps of the method for extracting the neuroimaging biomarker based on the interpretable ensemble 3DCNN according to Embodiment 1.

Embodiment 4

A computer device includes a storage medium, a processor, and a computer program stored in the medium and executable by the processor. The computer program, when executed by the processor, implements the steps of the method for extracting the neuroimaging biomarker based on the interpretable ensemble 3DCNN according to Embodiment 1.

Compared with the prior art, the present invention derives a novel neuroimaging biomarker P-score from prediction results obtained by the ensemble 3DCNN model. The solution may help researchers to conduct studies on longitudinal trajectory changes of sMRI images during the progression of Alzheimer's disease, and analyze an association of the longitudinal trajectory changes with neurodegenerative changes of Alzheimer's disease subjects. The extracted neuroimaging biomarker may provide a basis for predicting a sequence of intervention of brain regions in the neurodegenerative changes of an Alzheimer's disease patient and upcoming clinical symptoms.

Apparently, the above embodiments of the present invention are merely examples of the present invention for purposes of clarity and are not intended to limit the implementations of the present invention. Changes or modifications in other different forms may also be made by a person of ordinary skill in the art on the basis of the above description. All implementations need not to be, and cannot be, exhaustive. Any modifications, equivalent replacements, improvements, etc. made within the spirit and principle of the present invention shall fall within the scope of protection of the claims of the present invention.

What is claimed is:

1. A method for extracting a neuroimaging biomarker based on an interpretable ensemble three-dimensional convolutional neural network (3DCNN), comprising following steps:
   S1, acquiring an sMRI image to be processed, and preprocessing the sMRI image;
   S2, segmenting the preprocessed sMRI image into a plurality of 25×25×25 cubes;
   S3, inputting the 25×25×25 cubes into an ensemble 3DCNN model trained on a preset sMRI dataset to obtain a prediction probability of each of the 25×25×25 cubes as to whether the sMRI image belongs to an Alzheimer's disease patient; and
   S4, converting the prediction probability of each of the cubes into a neuroimaging biomarker P-score for the sMRI image;
   wherein the ensemble 3DCNN model comprises a plurality of base classifiers and a meta-classifier, wherein the base classifiers are 3DCNN models; and the meta-classifier comprises a one-dimensional convolutional layer and a fully connected layer in sequence,
   wherein a neuroimaging biomarker P-score$_{cube}$ of the sMRI image at a 25×25×25 cube level is obtained by:

$$P\text{-score}_{cube}(i,c) = w_{ic} \times p_{ic},$$

wherein i denotes an index of the sMRI image, c denotes an index of the 25×25×25 cube, $p_{ic}$ denotes the prediction probability as to whether the sMRI image belongs to an Alzheimer's disease patient obtained by a base classifier corresponding to the 25×25×25 cube (i, c), and w denotes a weight of the one-dimensional convolutional layer in the meta-classifier corresponding to the base classifier.

2. The method for extracting the neuroimaging biomarker based on the interpretable ensemble 3DCNN according to claim 1, wherein the preprocessing comprises skull extraction, MNI space registration, image smoothing, and image normalization.

3. The method for extracting the neuroimaging biomarker based on the interpretable ensemble 3DCNN according to claim 1, wherein a neuroimaging biomarker P-score$_{voxel}$ of the sMRI image at a voxel level is obtained by:
   evenly dividing, by voxels of a brain tissue in a 25×25×25 cube, P-score$_{cube}$ of the 25×25×25 cube where the voxels are located, that is, P-score$_{voxel}$=P-score$_{cube}$/M, wherein M denotes the quantity of the voxels of the brain tissue in the 25×25×25 cube; and setting a P-score$_{voxel}$ value of voxels of a non-brain tissue in the 25×25×25 cube to be 0.

4. The method for extracting the neuroimaging biomarker based on the interpretable ensemble 3DCNN according to claim 3, wherein a neuroimaging biomarker P-score$_{region}$ of the sMRI image at a brain region level is obtained by:

dividing a sum of P-score$_{voxel}$ of all voxels in the brain region by the quantity of the voxels comprised in the brain region.

5. The method for extracting the neuroimaging biomarker based on the interpretable ensemble 3DCNN according to claim 4, wherein a neuroimaging biomarker P-score$_{whole}$(i) of the sMRI image at a whole-brain level is obtained by:
scaling a value domain of P-score$_{region}$ of each brain region to a range of [0,1] by normalization; and aggregating the P-score$_{region}$ of each brain region after the normalization to obtain P-score$_{whole}$ of a whole-brain as follows:

$$P\text{-score}_{whole}(i)=\Sigma_k P\text{-score}_{region}(i,k),$$

wherein i denotes the index of the sMRI image, and k denotes an index of the brain region.

6. A system for extracting a neuroimaging biomarker based on an interpretable ensemble three-dimensional convolutional neural network (3DCNN), comprising an image acquisition and preprocessing module, an image segmentation module, a prediction probability acquisition module, and a prediction probability conversion module which are connected in sequence, wherein
the image acquisition and preprocessing module is configured to acquire an sMRI image to be processed and preprocess the sMRI image;
the image segmentation module is configured to segment the preprocessed sMRI image into a plurality of 25×25×25 cubes;
the prediction probability acquisition module is configured to input the 25×25×25 cubes into an ensemble 3DCNN model trained on a preset sMRI dataset to obtain a prediction probability of each of the 25×25×25 cubes as to whether the sMRI image belongs to an Alzheimer's disease patient; and
the prediction probability conversion module is configured to convert the prediction probability of each of the cubes into a neuroimaging biomarker P-score for the sMRI image;
wherein the ensemble 3DCNN model comprises a plurality of base classifiers and a meta-classifier, wherein the base classifiers are 3DCNN models; and the meta-classifier comprises a one-dimensional convolutional layer and a fully connected layer in sequence,
wherein a neuroimaging biomarker P-score$_{cube}$ of the sMRI image at a 25×25×25 cube level is obtained by:

$$P\text{-score}_{cube}(i,c)=w_{ic}\times p_{ic},$$

wherein i denotes an index of the sMRI image, c denotes an index of the 25×25×25 cube, $p_{ic}$ denotes the prediction probability as to whether the sMRI image belongs to an Alzheimer's disease patient obtained by a base classifier corresponding to the 25×25×25 cube (i, c), and w denotes a weight of the one-dimensional convolutional layer in the meta-classifier corresponding to the base classifier.

7. A storage medium having a computer program stored on the storage medium, wherein the computer program, when executed by a processor, implements the steps of the method for extracting the neuroimaging biomarker based on the interpretable ensemble 3DCNN according to claim 1.

8. A storage medium having a computer program stored on the storage medium, wherein the computer program, when executed by a processor, implements the steps of the method for extracting the neuroimaging biomarker based on the interpretable ensemble 3DCNN according to claim 2.

9. A storage medium having a computer program stored on the storage medium, wherein the computer program, when executed by a processor, implements the steps of the method for extracting the neuroimaging biomarker based on the interpretable ensemble 3DCNN according to claim 3.

10. A storage medium having a computer program stored on the storage medium, wherein the computer program, when executed by a processor, implements the steps of the method for extracting the neuroimaging biomarker based on the interpretable ensemble 3DCNN according to claim 4.

11. A storage medium having a computer program stored on the storage medium, wherein the computer program, when executed by a processor, implements the steps of the method for extracting the neuroimaging biomarker based on the interpretable ensemble 3DCNN according to claim 5.

12. A computer device, comprising a storage medium, a processor, and a computer program stored in the storage medium and executable by the processor, wherein the computer program, when executed by the processor, implements the steps of the method for extracting the neuroimaging biomarker based on the interpretable ensemble 3DCNN according to claim 1.

13. A computer device, comprising a storage medium, a processor, and a computer program stored in the storage medium and executable by the processor, wherein the computer program, when executed by the processor, implements the steps of the method for extracting the neuroimaging biomarker based on the interpretable ensemble 3DCNN according to claim 2.

14. A computer device, comprising a storage medium, a processor, and a computer program stored in the storage medium and executable by the processor, wherein the computer program, when executed by the processor, implements the steps of the method for extracting the neuroimaging biomarker based on the interpretable ensemble 3DCNN according to claim 3.

15. A computer device, comprising a storage medium, a processor, and a computer program stored in the storage medium and executable by the processor, wherein the computer program, when executed by the processor, implements the steps of the method for extracting the neuroimaging biomarker based on the interpretable ensemble 3DCNN according to claim 4.

16. A computer device, comprising a storage medium, a processor, and a computer program stored in the storage medium and executable by the processor, wherein the computer program, when executed by the processor, implements the steps of the method for extracting the neuroimaging biomarker based on the interpretable ensemble 3DCNN according to claim 5.

* * * * *